US011610140B2

(12) United States Patent
Graf et al.

(10) Patent No.: US 11,610,140 B2
(45) Date of Patent: Mar. 21, 2023

(54) PREDICTING FATIGUE OF AN ASSET THAT HEALS

(71) Applicant: General Electric Company, Schenectady, NY (US)

(72) Inventors: Alexander Graf, San Ramon, CA (US); David Sulkin, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 1119 days.

(21) Appl. No.: 16/233,474

(22) Filed: Dec. 27, 2018

(65) Prior Publication Data

US 2020/0210859 A1 Jul. 2, 2020

(51) Int. Cl.
  *G06N 20/00* (2019.01)
  *G09G 5/00* (2006.01)
  *G06N 5/04* (2023.01)
  *G06F 3/01* (2006.01)
  *G16H 50/30* (2018.01)

(52) U.S. Cl.
  CPC .............. *G06N 5/04* (2013.01); *G06F 3/015* (2013.01); *G06N 20/00* (2019.01); *G16H 50/30* (2018.01); *G06F 2203/011* (2013.01)

(58) Field of Classification Search
  CPC .......... G06N 5/04; G06N 20/00; G16H 50/30; G16H 80/00; G06F 3/015; G06F 220/011; G09G 5/00; A61B 5/165; A61B 5/01; A61B 5/7282; A61B 5/4857
  See application file for complete search history.

(56) References Cited

U.S. PATENT DOCUMENTS

| | | | |
|---|---|---|---|
| 2016/0174890 A1* | 6/2016 | Ko ....................... | A61B 5/6893 340/576 |
| 2018/0056131 A1* | 3/2018 | Nakazawa ......... | A63B 71/0622 |
| 2018/0156197 A1* | 6/2018 | Spruce .................. | F03D 7/0292 |
| 2018/0203949 A1* | 7/2018 | Hagen ................. | G01M 5/0025 |

* cited by examiner

*Primary Examiner* — Pegeman Karimi
(74) *Attorney, Agent, or Firm* — Buckley, Maschoff & Talwalkar LLC (57) ABSTRACT

The example embodiments are directed to a system and method which can predict a degradation in the health of an asset that heals based on data sensed from a machine or equipment operated by the asset that heals and in consideration of healing of the asset. In one example, a method may include one or more of storing time-series data of an operation of a machine, predicting a fatigue value of an operator of the machine via a predictive model that comprises a Rainflow counting algorithm that determines a degradation of the operator based on a changing attribute in the time-series data and a healing function that determines a healing component of the operator based on rest of the operator, and outputting information about the predicted fatigue value via a user interface.

18 Claims, 6 Drawing Sheets

PREDICTING FATIGUE OF AN ASSET THAT HEALS

BACKGROUND

Machine and equipment assets are engineered to perform particular tasks as part of a process. For example, assets can include, among other things, industrial manufacturing equipment on a production line, drilling equipment for use in mining operations, wind turbines that generate electricity on a wind farm, transportation vehicles (trains, subways, airplanes, etc.), gas and oil refining equipment, and the like. As another example, assets may include devices that aid in diagnosing patients such as imaging devices (e.g., X-ray or MRI systems), monitoring equipment, and the like. The design and implementation of these assets often takes into account both the physics of the task at hand, as well as the environment in which such assets are configured to operate.

Low-level software and hardware-based controllers have long been used to drive machine and equipment assets. However, the overwhelming adoption of cloud computing, increasing sensor capabilities, and decreasing sensor costs, as well as the proliferation of mobile technologies, have created opportunities for creating novel industrial and healthcare based assets with improved sensing technology and which are capable of transmitting data that can then be distributed throughout a network. As a consequence, there are new opportunities to enhance the business value of some assets through the use of novel industrial-focused hardware and software.

Industrial assets such as aircraft, locomotives, trucks, drilling/mining equipment, submersibles, and the like, often require an operator to control the machine or equipment to ensure that operations are correct and run smoothly. Over time, just like the industrial assets, the operator themselves can become fatigued due to the forces (strain, pressure, temperature, etc.) that is caused by a machine to the human body. Monitoring the health of an operator, however, is difficult to do without acquiring sensitive health information of the user. Health data, however is protected and is not typically divulged to a company, client, etc. which employs the operator. Therefore, determining a health of the operator can be a very difficult task. Accordingly, what is needed is a mechanism which can predict fatigue to an operator without relying on sensitive health information.

SUMMARY

The embodiments herein improve upon the prior art by providing a system which can determine fatigue of an asset that heals (e.g., human, animal, etc.) based on time-series data captured of a machine and without access or need for health data of the asset that heals. As an example, the system an determine the fatigue of an operator of a machine/equipment such as a locomotive, an aircraft, a healthcare machine, mining/drilling equipment, a truck, a subway, and the like. A predictive model may be run on the machine data to determine a degradation of the asset that includes. For example, the predictive model may include a Rainflow counting algorithm that is executed based on machine data that is captured and fed into the system. The Rainflow counting algorithm may predict a degradation component of the asset that heals based on the machine data associated with the asset. Furthermore, the predictive model may also include a healing function that generates a healing component of the asset that heals. The healing function may be based on rest or non-operation of the operator and may reduce the degradation predicted by the Rainflow counting algorithm.

In an aspect of an example embodiment, a computing system may include one or more of a storage configured to store time-series data of an operation of a machine, and a processor configured to predict a fatigue value of an operator of the machine via a predictive model that comprises a Rainflow counting algorithm that determines a degradation of the operator based on a changing attribute in the time-series data and a healing function that determines a healing component of the operator based on non-operation of the machine, wherein the processor is further configured to output information about the predicted fatigue value via a user interface.

In an aspect of another example embodiment, a method may include one or more of storing time-series data of an operation of a machine, predicting a fatigue value of an operator of the machine via a predictive model that comprises a Rainflow counting algorithm that determines a degradation of the operator based on a changing attribute in the time-series data and a healing function that determines a healing component of the operator based on non-operation of the machine, and outputting information about the predicted fatigue value via a user interface.

Other features and aspects may be apparent from the following detailed description taken in conjunction with the drawings and the claims.

BRIEF DESCRIPTION OF THE DRAWINGS

Features and advantages of the example embodiments, and the manner in which the same are accomplished, will become more readily apparent with reference to the following detailed description taken in conjunction with the accompanying drawings.

Throughout the drawings and the detailed description, unless otherwise described, the same drawing reference numerals will be understood to refer to the same elements, features, and structures. The relative size and depiction of these elements may be exaggerated or adjusted for clarity, illustration, and/or convenience.

DETAILED DESCRIPTION

In the following description, specific details are set forth in order to provide a thorough understanding of the various example embodiments. It should be appreciated that various modifications to the embodiments will be readily apparent to those skilled in the art, and the generic principles defined herein may be applied to other embodiments and applications without departing from the spirit and scope of the disclosure. Moreover, in the following description, numerous details are set forth for the purpose of explanation. However, one of ordinary skill in the art should understand that embodiments may be practiced without the use of these specific details. In other instances, well-known structures and processes are not shown or described in order not to obscure the description with unnecessary detail. Thus, the present disclosure is not intended to be limited to the embodiments shown, but is to be accorded the widest scope consistent with the principles and features disclosed herein.

The example embodiments are directed to a system which can predict a health value (e.g., degradation in health) of an asset with healing capabilities (e.g., a human, an animal, etc.) using machine data which is associated with the asset. For example, the system can predict a fatigue value of an operator of an industrial machine or equipment based on sensor data acquired from an operation of the machine or equipment. Examples of machines that can be considered include, but are not limited to, aircraft, boats, locomotives, subways, mining equipment, drilling equipment, power equipment (drills, saws, jackhammers, etc.). The machine may have one or more sensors that are attached to it or in a surrounding environment for sensing time-series data associated with the machine over time such as pressure, temperature, humidity, velocity, strain, force, and the like. Using a modified Rainflow counting model, the system can predict a health value of a user over time.

Traditional degradation monitoring for structures such as machine or equipment may be performed through Rainflow counting where an algorithm keeps track of oscillations in a sister value (number of oscillations) as well as the magnitude of oscillations and determines a degradation of the machine based thereon. For example, a paper clip is bent back and forth, at some point its going to break. However, if the damage to the paper clip is stopped halfway it won't break but it is still worn out to some extent which is captured by the classical form of Rainflow counting. Similarly, for industrial machines, the degradation grows over time (never decays) and when the degradation reaches a threshold, an operator may consider it a failure or other event (maintenance, repair, inspection, etc.).

The example embodiments apply a similar degradation monitoring (fatigue, stress, etc.) to living beings (such as humans, animals, etc.). Examples include pilots of an aircraft, operators of a locomotive, drivers of a truck, etc. The system may not have information on the individuals themselves because of privacy issues. In other words, while medical records can provide more direct measurements, this information is typically confidential. Instead, the example embodiments use Rainflow counting to determine the degradation of a human. However, instead of continuously detecting degradation, the predictive model also includes a healing component (i.e., a decay of the degradation) which represents the healing of the human. The system may use a rolling window of time (e.g., 1 minute, 1 hour, 1 day, 1 week, etc.) instead of the metric that continually increases over time. For example, if the machine has a downtime, and the operator gets to relax or repair themselves, the metric decreases. The system incorporates a rolling window plus a decay factor for healing. The rolling window captures events over a predetermined period of time (specific start point and a specific end point) rather than a continual degradation metric like with machine/equipment.

Rainflow counting has been used to predict degradation in assets such as machine and equipment. These traditional models usually rely on a continuously increasing damage/fatigue to the asset which does not go the other way. In other words, the machines/equipment cannot recover from the damage/fatigue. In contrast, an asset that heals such as a person can improve their health over time when not operating the machine or equipment. To address the recovery aspects of a human, the example embodiments incorporate a healing component into the Rainflow counting model which can be used to adjust the fatigue/damage created by the machine with a healing factor based on rest and recover of a human, etc.

The system described herein may be implemented via a module or other software that may be used in conjunction with applications for managing machine and equipment assets hosted within an industrial interne of things (IIoT). An IIoT may connect assets, such as turbines, jet engines, locomotives, elevators, healthcare devices, mining equipment, oil and gas refineries, and the like, to the Internet or a cloud computing system, or to each other in some meaningful way such as through one or more networks. The cloud can be used to receive, relay, transmit, store, analyze, or otherwise process information for or about assets and manufacturing sites. In an example, the cloud computing system includes at least one processor circuit, at least one database, and a plurality of users and/or assets that are in data communication with the cloud computing system. The cloud computing system can further include or can be coupled with one or more other processor circuits or modules configured to perform a specific task, such as to perform tasks related to asset maintenance, analytics, data storage, security, or some other function.

Assets may be outfitted with one or more sensors (e.g., physical sensors, virtual sensors, etc.) configured to monitor respective operations or conditions of the asset and the environment in which the asset operates. Sensors can be placed on an asset, in an asset, around an asset (in a surrounding environment), and the like. In some examples, the asset may be a virtual asset that is monitored through a virtual simulation. The virtual asset may be configured with virtual sensors. Data from the sensors can be recorded or transmitted to a cloud-based or other remote computing environment. By bringing such data into a cloud-based computing environment, new software applications informed by industrial process, tools and know-how can be constructed, and new physics-based analytics specific to an industrial environment can be created. Insights gained through analysis of such data can lead to enhanced asset designs, enhanced software algorithms for operating the same or similar assets, better operating efficiency, and the like.

While progress with industrial and machine automation has been made over the last several decades, and assets have become 'smarter,' the intelligence of any individual asset pales in comparison to intelligence that can be gained when multiple smart devices are connected together, for example, in the cloud. Aggregating data collected from or about multiple assets can enable users to improve business processes, for example by improving effectiveness of asset maintenance or improving operational performance if appropriate industrial-specific data collection and modeling technology is developed and applied.

The integration of machine and equipment assets with the remote computing resources to enable the IIoT often presents technical challenges separate and distinct from the specific industry and from computer networks, generally. To address these problems and other problems resulting from the intersection of certain industrial fields and the IIoT, the example embodiments provide a mechanism for cross-pollination of features across different industrial domains.

An Asset Management Platform (AMP) technology may rely on cloud computing techniques that enable incorporation of a manufacturer's asset knowledge with a set of development tools and best practices that enables asset users to bridge gaps between software and operations to enhance capabilities, foster innovation, and ultimately provide economic value. Through the use of such a system, a manufacturer of industrial or healthcare based assets can be uniquely situated to leverage its understanding of assets themselves, models of such assets, and industrial operations or applications of such assets, to create new value for industrial customers through asset insights. The system described herein may be incorporated within an AMP or other cloud environment.

Figure 1:
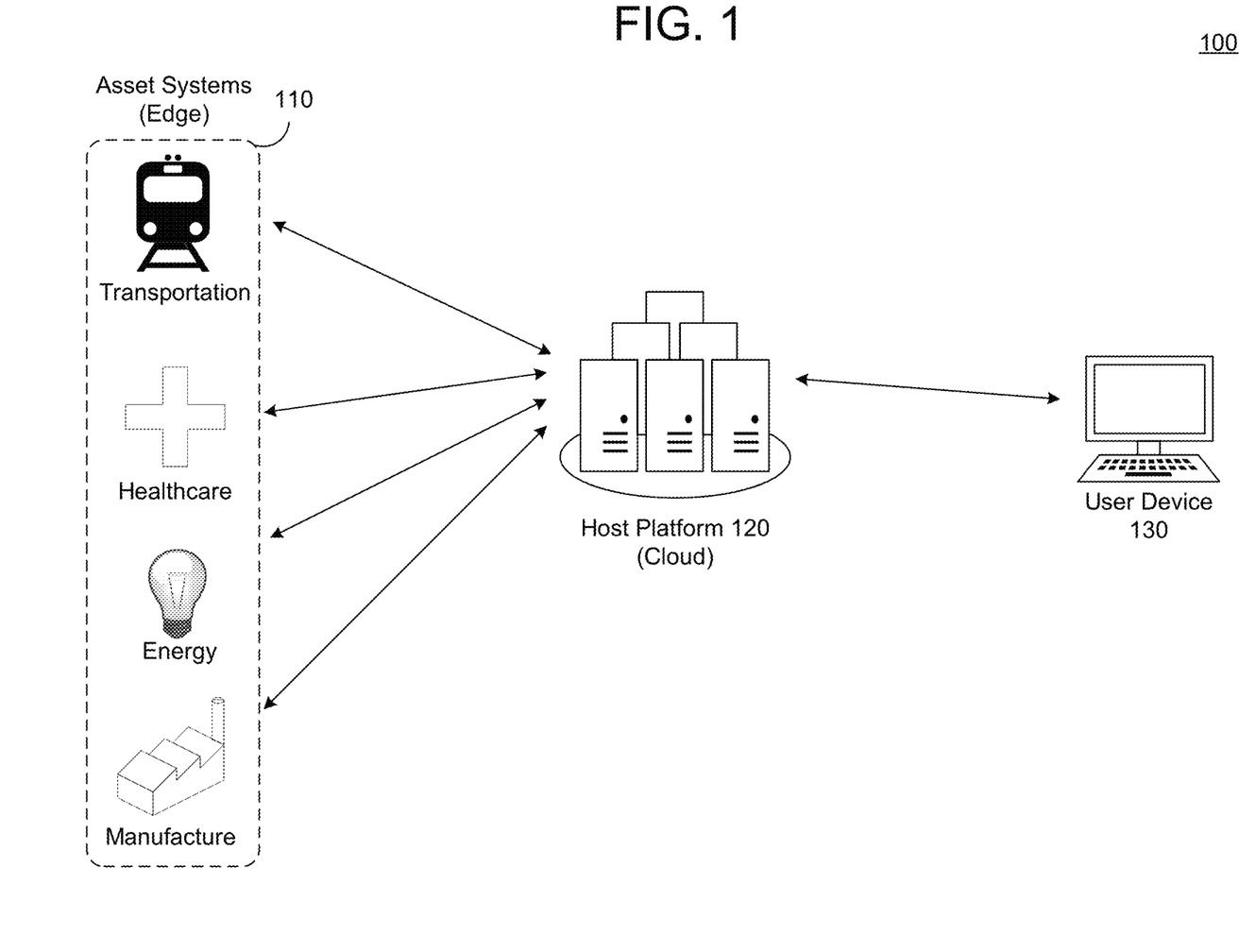
FIG. 1 is a diagram illustrating an industrial cloud computing environment for machine learning in accordance with an example embodiment.

FIG. 1 illustrates a cloud computing system 100 for industrial software and hardware in accordance with an example embodiment. Referring to FIG. 1, the system 100 includes a plurality of assets 110 which may be included within an edge of an IIoT and which may transmit raw data to a source such as cloud computing platform 120 where it may be stored and processed. It should also be appreciated that the cloud platform 120 in FIG. 1 may be replaced with or supplemented by a non-cloud based platform such as a server, an on-premises computing system, and the like. Assets 110 may include hardware/structural assets such as machine and equipment used in industry, healthcare, manufacturing, energy, transportation, and that like. It should also be appreciated that assets 110 may include software, processes, actors, resources, and the like. A digital replica (i.e., a digital twin) of an asset 110 may be generated and stored on the cloud platform 120. The digital twin may be used to virtually represent (virtual asset) an operating characteristic of the asset 110.

The data transmitted by the assets 110 and received by the cloud platform 120 may include raw time-series data output as a result of the operation of the assets 110, and the like. Data that is stored and processed by the cloud platform 120 may be output in some meaningful way to user devices 130. In the example of FIG. 1, the assets 110, cloud platform 120, and user devices 130 may be connected to each other via a network such as the Internet, a private network, a wired network, a wireless network, etc. Also, the user devices 130 may interact with software hosted by and deployed on the cloud platform 120 in order to receive data from and control operation of the assets 110.

Software and hardware systems can be used to enhance or otherwise in conjunction with the operation of an asset and a digital twin of the asset (and/or other assets), may be hosted by the cloud platform 120, and may interact with the assets 110. For example, ML models (or AI models) may be used to optimize a performance of an asset or data coming in from the asset. As another example, the ML models may be used to predict, analyze, control, manage, or otherwise interact with the asset and components (software and hardware) thereof. The ML models may also be stored in the cloud platform 120 and/or at the edge (e.g. asset computing systems, edge PC's, asset controllers, etc.)

The user device 130 may receive views of data or other information about the asset as the data is processed via one or more applications hosted by the cloud platform 120. For example, the user device 130 may receive graph-based results, diagrams, charts, warnings, measurements, power levels, and the like. As another example, the user device 130 may display a graphical user interface that allows a user thereof to input commands to an asset via one or more applications hosted by the cloud platform 120. According to various embodiments, the graph-based results may include a display of health data patterns of a user, operator, etc. associated with an asset (e.g., industrial machine or equipment, etc.)

In some embodiments, an asset management platform (AMP) can reside within or be connected to the cloud platform 120, in a local or sandboxed environment, or can be distributed across multiple locations or devices and can be used to interact with the assets 110. The AMP can be configured to perform functions such as data acquisition, data analysis, data exchange, and the like, with local or remote assets, or with other task-specific processing devices. For example, the assets 110 may be an asset community (e.g., turbines, healthcare, power, industrial, manufacturing, mining, oil and gas, elevator, etc.) which may be communicatively coupled to the cloud platform 120 via one or more intermediate devices such as a stream data transfer platform, database, or the like.

Information from the assets 110 may be communicated to the cloud platform 120. For example, external sensors can be used to sense information about a function, process, operation, etc., of an asset, or to sense information about an environment condition at or around an asset, a worker, a downtime, a machine or equipment maintenance, and the like. The external sensor can be configured for data communication with the cloud platform 120 which can be configured to store the raw sensor information and transfer the raw sensor information to the user devices 130 where it can be accessed by users, applications, systems, and the like, for further processing. Furthermore, an operation of the assets 110 may be enhanced or otherwise controlled by a user inputting commands though an application hosted by the cloud platform 120 or other remote host platform such as a web server. The data provided from the assets 110 may include time-series data or other types of data associated with the operations being performed by the assets 110

In some embodiments, the cloud platform 120 may include a local, system, enterprise, or global computing infrastructure that can be optimized for industrial data workloads, secure data communication, and compliance with regulatory requirements. The cloud platform 120 may include a database management system (DBMS) for creating, monitoring, and controlling access to data in a database coupled to or included within the cloud platform 120. The cloud platform 120 can also include services that developers can use to build or test industrial or manufacturing-based applications and services to implement IIoT applications that interact with assets 110.

For example, the cloud platform 120 may host an industrial application marketplace where developers can publish their distinctly developed applications and/or retrieve applications from third parties. In addition, the cloud platform 120 can host a development framework for communicating with various available services or modules. The development framework can offer developers a consistent contextual user experience in web or mobile applications. Developers can add and make accessible their applications (services, data, analytics, etc.) via the cloud platform 120. Also, analytic software may analyze data from or about a manufacturing process and provide insight, predictions, and early warning fault detection.

Figure 2:
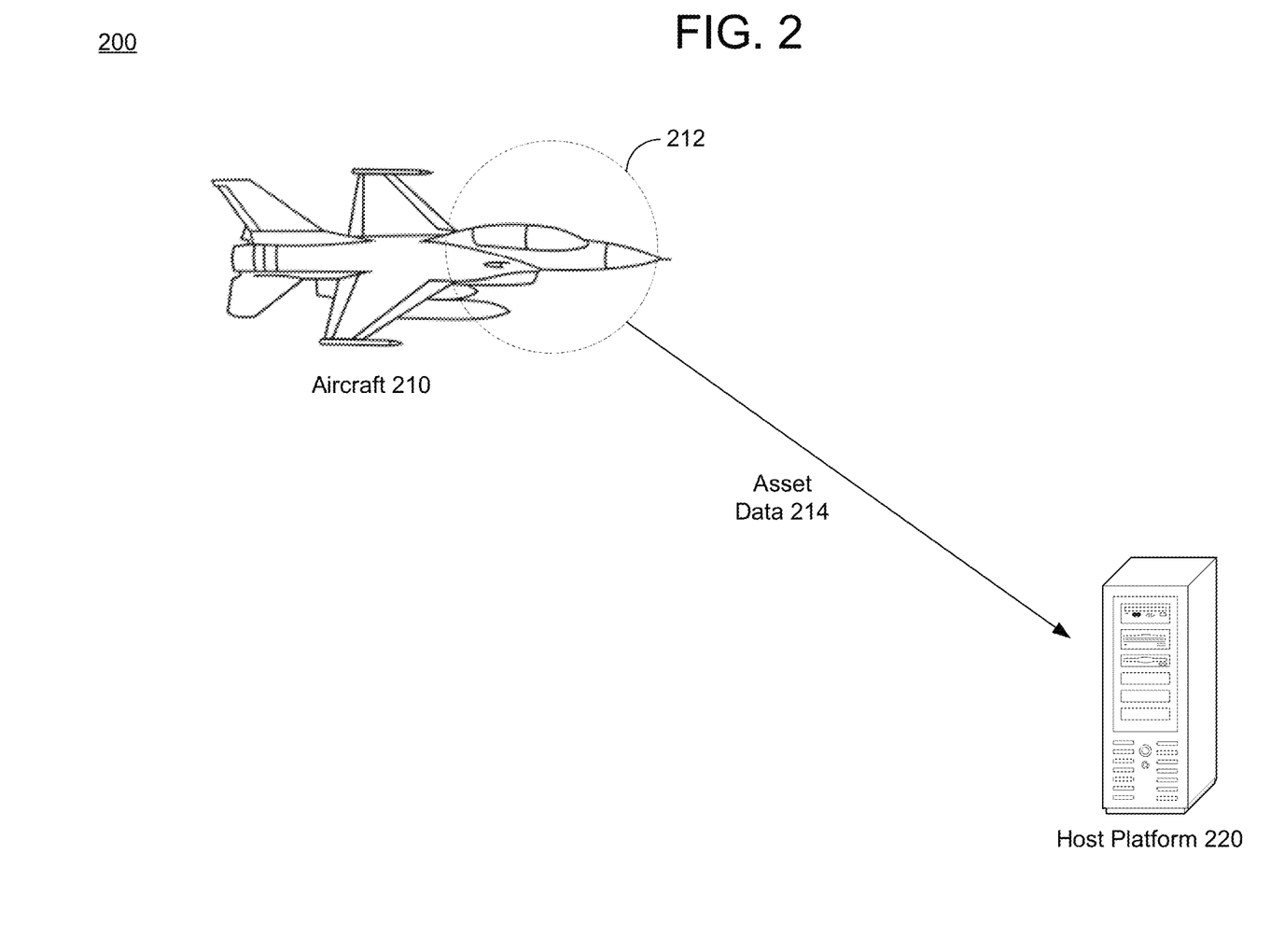
FIG. 2 is a diagram illustrating a communication system in which machine asset data is transmitted to a host platform in accordance with an example embodiment.

FIG. 2 illustrates a communication system 200 in which asset data 214 is transmitted to a host platform 220 in accordance with an example embodiment. Referring to the example shown in FIG. 2, the communication system 200 includes an asset 210 which includes one or more sensors providing asset data 214 to the host platform 220. The asset 210 in this example includes an aircraft. The asset 210 may include any machine or equipment in which fatigue may include to an operator thereof such as a locomotive, an aircraft, a boat, a ship, oil equipment, drilling/mining equipment, or the like. The asset data 214 may include time-series data that is captured by one or more sensors such as pressure, temperature, altitude, humidity, rotation, strain, and the like. The asset data 214 may include data that can be used to determine a fatigue value of an operator of the asset 210.

In the example of FIG. 2, the asset data 214 may include temperature, pressure, velocity, etc., which is associated with or sensed by sensors located within a cockpit 212 of the asset 210. The asset data 214 may identify conditions within an environment where an operator of the asset 210 is positioned during a flight. The asset data 214 may be transmitted in real-time during the flight, or it may be provided after-the-fact such as during a download from a computer system on the asset 210 to the host platform 220. Here, the asset 210 may include sensors such as humidity, temperature, pressure, etc., which capture data and store the data in a computing system in the asset 210. The sensor data may be transmitted to the host platform 220 via a network such as the Internet, satellite, and the like. It is not a requirement that the asset data 210 be positioned in and around the cockpit 212 or other user environment. The asset data 210 may include any data associated with the asset 210 that is sensed from the asset 210 or based on an environment of the asset 210.

Figure 3A:
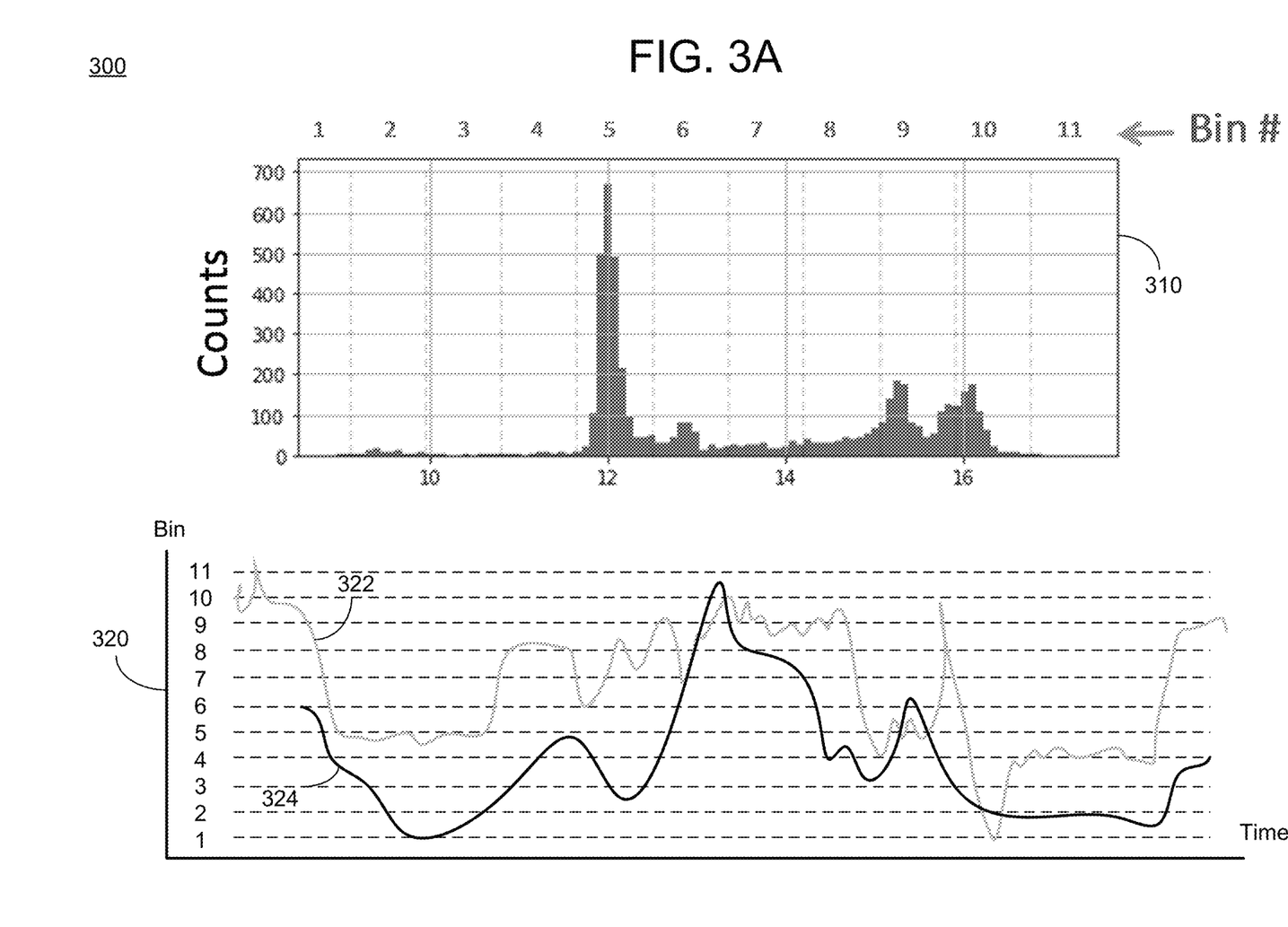
FIGS. 3A-3B are diagrams illustrating the predictive model for an asset that heals in accordance with an example embodiment.
Figure 3B:
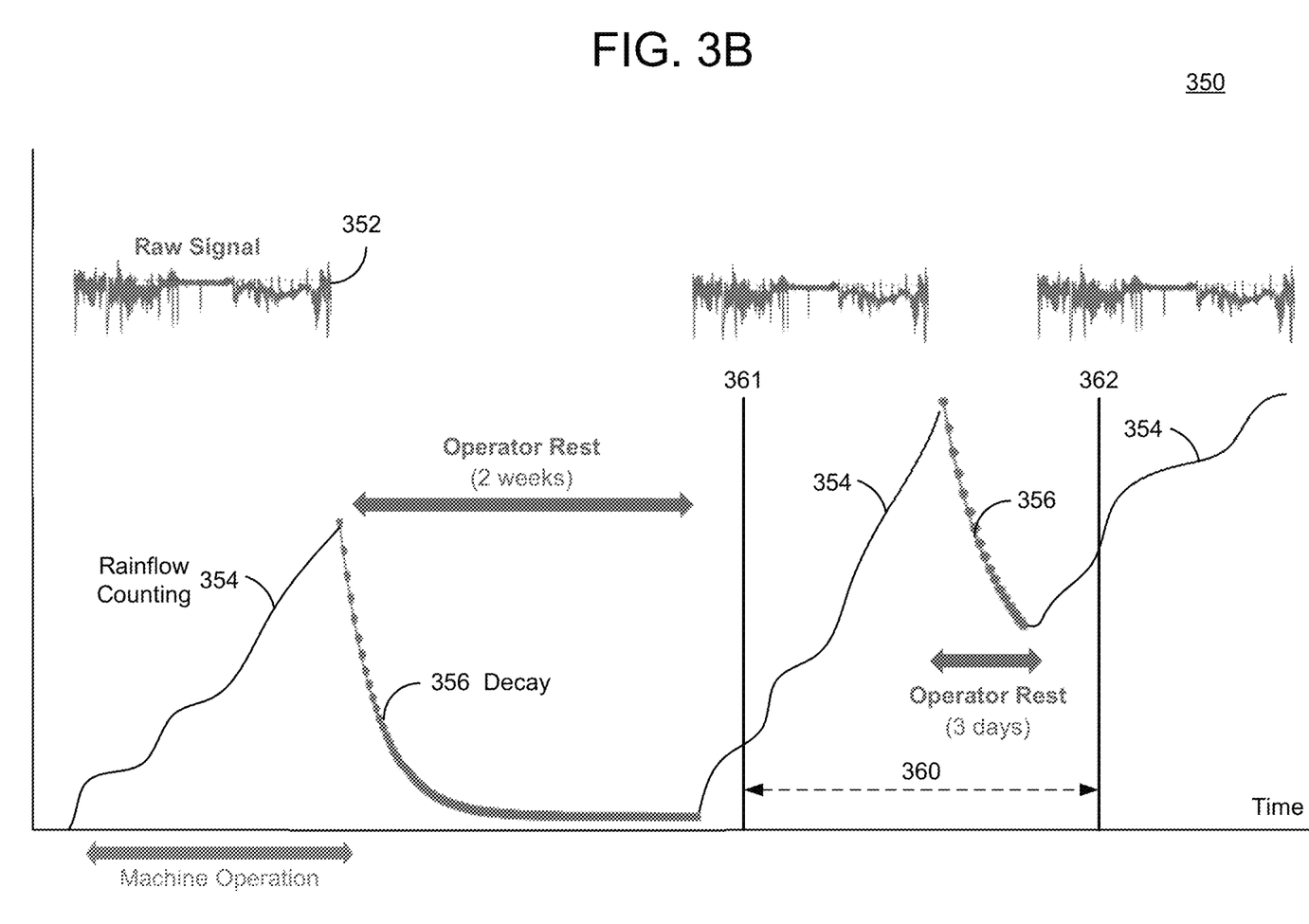

FIG. 3A illustrates a user interface 300 which includes a graph 310 of bin information generated from asset data, and a graph 320 that includes a raw sensor data value 322 of an asset and a fatigue value 324 of an asset that heals. For example, the fatigue value 322 may be associated with an asset such as a machine or equipment used in industry, manufacture, healthcare, or the like and the fatigue value 324 may be associated an operator of the machine or equipment. Meanwhile, FIG. 3B illustrates a graph 350 generated by execution of a predictive model. The graph 350 includes degradation components 354 determined by a Rainflow counting algorithm of the predictive model based on asset data 352 and healing components 356 determined by a decay function of the predictive model based on periods of rest of the operator.

Referring to FIGS. 3A and 3B, Rainflow counting can be used to keep track of a number of oscillations in a sister value of asset data over time and a magnitude of such oscillations. The sister value may correspond to an attribute of the asset data. For example, in the case of an aircraft, altitude may be measured by a sensor and analyzed to keep track of oscillations in the altitude. For industrial equipment, the oscillations continue over time and cause a degradation/fatigue value predicted by the Rainflow counting to grow over time (never decay). This is because industrial assets do not heal. In a typical asset environment, when the degradation reaches a threshold, the system may output an alert indicating that maintenance, repair, inspection, or the like, is needed. The example embodiments adapt this same degradation monitoring to living beings (such as humans, animals, etc.). Examples include pilots of an aircraft, operators of a locomotive, drivers of a truck, etc. The system does not need health data of the individuals themselves because of privacy issues. Medical records can provide more direct measurements, but this information is confidential.

The example embodiments use a predictive model that includes a Rainflow counting algorithm to determine the degradation of a human. However, instead of continuously detecting degradation, the predictive model also includes a decay function (i.e., decay of the degradation detected by the Rainflow counting) which represents the healing of the individual. The embodiments may use a rolling window 360 such as shown in the example of FIG. 3B, where instead of the metric just increasing continually over time, if there's a downtime, and the operator gets to relax or repair themselves, the metric decreases. The rolling window 360 includes a specific beginning point 361 in time and a specific end point 362 in time. That is, the rolling window 360 captures events over a predetermined period of time (specific start point and a specific end point) rather than a continual degradation metric like with machine/equipment.

In FIG. 3A, the raw sensor data represented by trace 322 represents altitude values of the aircraft as it goes up and down within the real world over time. Meanwhile, the fatigue value of the operator represented by trace 324 is the transformation of a rolling Rainflow counting metric for some choice of window size. The window size may be dynamically set based on preference of a user of the system, or the like. In the top graph 310, the total distribution of the altitude measurements over a period of time is split into bins. For example, the distribution of the altitude is split into 11 bins. The Rainflow counting algorithm may keep track of changes in altitude between bins such as when the aircraft goes from bin A and bin B (or whatever combination of bins). These are the oscillations depending on which bin it turns around in which captures the magnitude. The bins in this example represent buckets of altitude. If you go from bin 1 to bin 2 that's less magnitude that bin 1 to bin 5, etc. The oscillations are changes in altitude. The raw sensor data represented by trace 322 represents the changes in altitude. The changes correspond to "oscillations" within the Rainflow counting algorithm. Bin 1 to Bin 2 would be counted differently than Bin 2 to Bin 3. As the fatigue value (trace 324) goes up the pilot is being worn out and as it goes down the pilot is recovering.

The bins may be arbitrarily set and may be used to measure fatigue based on a Rainflow counting algorithm. FIG. 3B illustrates an example of a predictive model that generates fatigue components 354 measured based on a Rainflow counting algorithm of the predictive model which transforms a raw sensor signal 352 into the fatigue components 354. The predictive model also generates healing components 356 measured by a decay function of the predictive model. The decay function may be an exponential decay, or the like. In between operating periods of the machine, the operator may rest, sleep, etc., thereby creating a healing effect for the operator. This healing can be simulated through the use of the healing function of the predictive model which reduces or otherwise degrades the fatigue value generated by the Rainflow counting algorithm. For example, you can use a random exponential decay to represent the healing of the operator, but it depends on what you are applying to.

Figure 4:
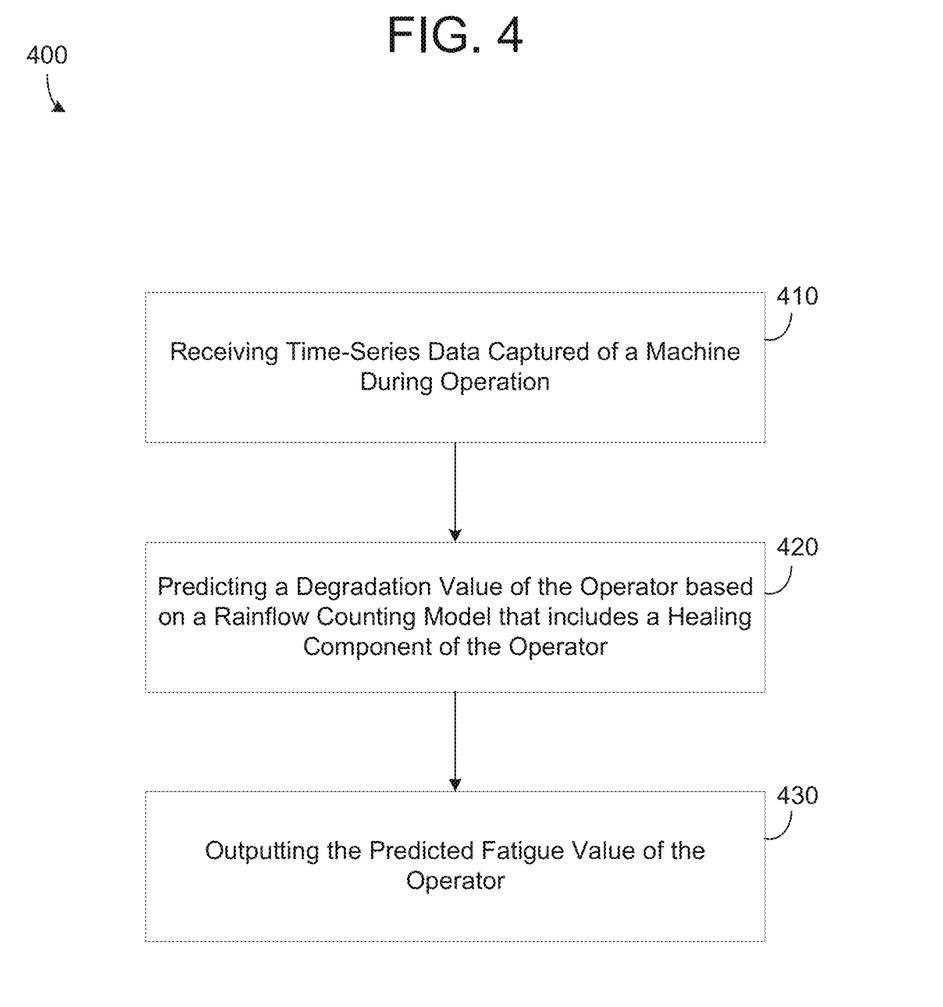
FIG. 4 is a diagram illustrating a method for determining a health value of an asset that heals in accordance with an example embodiment.

FIG. 4 illustrates a method 400 for determining a health value of an asset that heals in accordance with an example embodiment. For example, the method 400 may be performed by a computing system such as a server (e.g., a web server, etc.), a user device, a cloud platform, a database, and the like. In some embodiments, the method 400 may be performed by a single device or multiple devices working together. Referring to FIG. 4, in 410, the method may include storing time-series data of an operation of a machine. For example, the machine may include an aircraft, a locomotive, an automotive vehicle, a submersible, a ship, an equipment for use in drilling or mining, a healthcare machine, and the like. In some cases, the machine may include a plurality of machines and/or equipment. The time-series data may include one or more of temperature, pressure, altitude, velocity, humidity, and noise, which are captured of the machine during operation. In some embodiments, a single attribute of the time-series data may be used. As another example, multiple attributes of the time-series data may be evaluated.

In 420, the method may include predicting a fatigue value of an operator of the machine via a predictive model that includes a Rainflow counting algorithm that determines a degradation of the operator based on a changing attribute in the time-series data and a healing function that determines a healing component of the operator based on rest of the operator. The changing attribute may include a change in time-series value over time. In some embodiments, the predictive model may be executed based on a rolling window of the time-series data. In some embodiments, the healing component may create a reduction in the degradation of the operator based on the non-operating time of the machine, rest of the user, or the like. In some embodiments, the predictive may include determining the degradation of the operator based on magnitudes of oscillations in the time-series data of the machine. In some embodiments, the predicting the fatigue value comprises applying a decay function representing healing of the operator to the degradation of the operator determined by the Rainflow counting algorithm.

In 430, the method may include outputting information about the predicted fatigue value via a user interface. For example, the outputting may include outputting a graphical pattern of the predicted fatigue value over time which identifies the degradation and the healing component of the operator. In some embodiments, a metric of the health of the user such as a score, a letter grade, a warning, an alert, or the like, may be output based on changes in the predicted health of the user/operator. For example, if the operator's health drops below a preset threshold, the system may output a warning or a color-coded signal indicating detrimental health.

Figure 5:
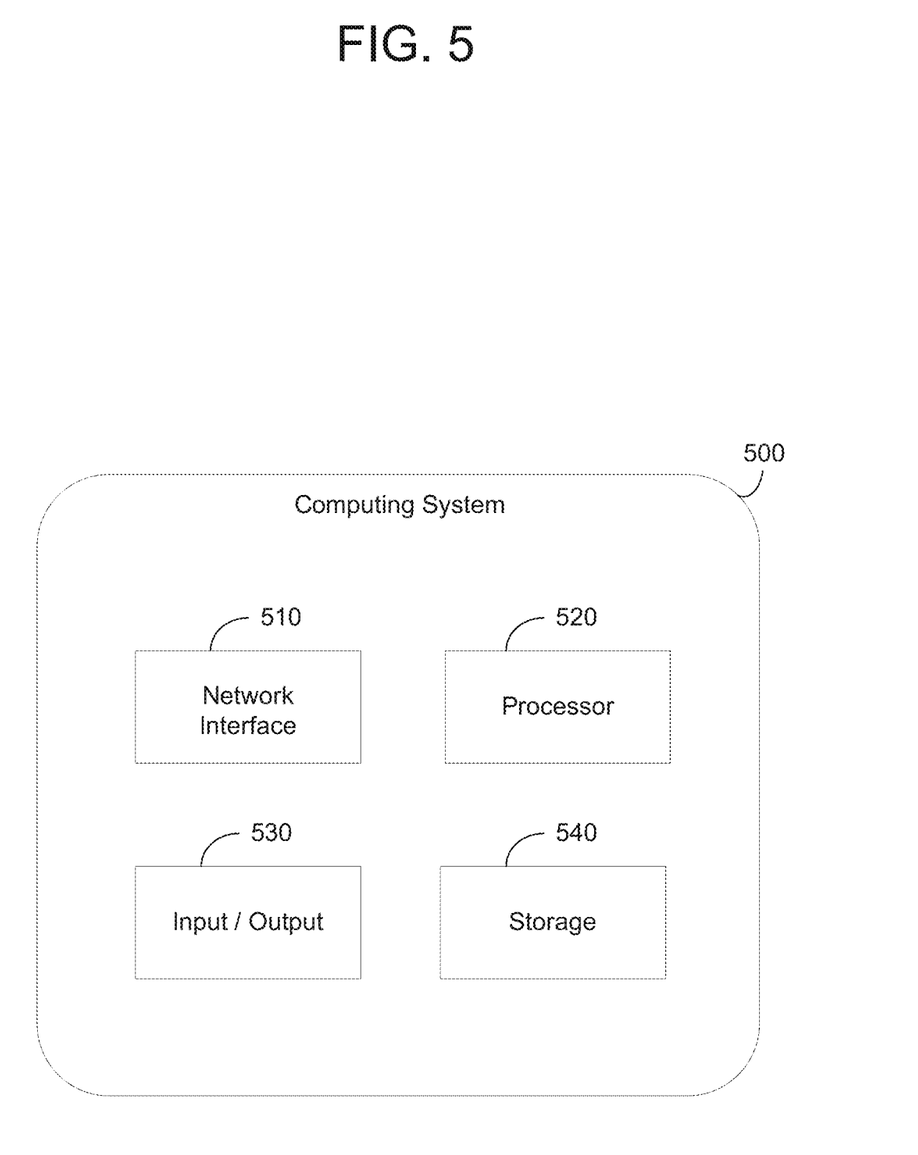
FIG. 5 is a diagram illustrating a computing system for use with any of the example embodiments.

FIG. 5 illustrates a computing system 500 for determining a service contract renewal propensity in accordance with an example embodiment. For example, the computing system 500 may be a cloud platform, a server, a user device, or some other computing device with a processor. Also, the computing system 500 may perform the method of FIG. 4. Referring to FIG. 5, the computing system 500 includes a network interface 510, a processor 520, an input/output 530, and a storage device 540. Although not shown in FIG. 5, the computing system 500 may include other components such as a display, a microphone, a receiver/transmitter, and the like. In some embodiments, the processor 520 may be used to control or otherwise replace the operation of any of the components of the computing system 500.

The network interface 510 may transmit and receive data over a network such as the Internet, a private network, a public network, and the like. The network interface 510 may be a wireless interface, a wired interface, or a combination thereof. The processor 520 may include one or more processing devices each including one or more processing cores. In some examples, the processor 520 is a multicore processor or a plurality of multicore processors. The input/output 530 may be a hardware device that includes one or more of a port, an interface, a cable, etc., that can receive data input and output data to (e.g., to an embedded display of the device 500, an externally connected display, an adjacent computing device, a cloud platform, a printer, an input unit, and the like. The storage device 540 is not limited to any particular storage device and may include any known memory device such as RAM, ROM, hard disk, and the like.

According to various embodiments, the network interface 510 may receive time-series data of an operation of a machine, and the time-series data may be stored in the storage 540. The processor 520 may predict a fatigue value of an operator of the machine via a predictive model that comprises a Rainflow counting algorithm that determines a degradation of the operator based on a changing attribute in the time-series data and a healing function that determines a healing component of the operator based on rest of the operator. Furthermore, the processor 520 may output information about the predicted fatigue value via a user interface. According to various embodiments, the predictive model may be executed based on a rolling window of time-series data.

In some embodiments, the machine may include one of an aircraft, a locomotive, an automotive vehicle, a submersible, a ship, an equipment for use in drilling or mining, and a healthcare machine. In some embodiments, the time-series data may include one or more of temperature, pressure, altitude, velocity, humidity, and noise, which are captured of the machine during operation. In some embodiments, the healing component may include a reduction in the degradation of the operator based on the non-operating time of the machine. In some embodiments, the processor 520 may predict the fatigue value by applying a decay function representing healing of the operator to the degradation of the operator determined by the Rainflow counting algorithm. In some embodiments, the processor 520 may output a graphical pattern of the predicted fatigue value over time which identifies the degradation and the healing component of the operator. In some embodiments, the processor 520 may determine the degradation of the operator based on magnitudes of oscillations in the time-series data of the machine.

As will be appreciated based on the foregoing specification, the above-described examples of the disclosure may be implemented using computer programming or engineering techniques including computer software, firmware, hardware or any combination or subset thereof. Any such resulting program, having computer-readable code, may be embodied or provided within one or more non transitory computer-readable media, thereby making a computer program product, i.e., an article of manufacture, according to the discussed examples of the disclosure. For example, the non-transitory computer-readable media may be, but is not limited to, a fixed drive, diskette, optical disk, magnetic tape, flash memory, semiconductor memory such as read-only memory (ROM). The article of manufacture containing the computer code may be made and/or used by executing the code directly from one medium, by copying the code from one medium to another medium, or by transmitting the code over a network.

The computer programs (also referred to as programs, software, software applications, "apps", or code) may include machine instructions for a programmable processor, and may be implemented in a high-level procedural and/or object-oriented programming language, and/or in assembly/machine language. As used herein, the terms "machine-readable medium" and "computer-readable medium" refer to a computer program product, apparatus, and/or device (e.g., magnetic discs, optical disks, memory, programmable logic devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal that may be used to provide machine instructions and/or any other kind of data to a programmable processor.

The above descriptions and illustrations of processes herein should not be considered to imply a fixed order for performing the process steps. Rather, the process steps may be performed in any order that is practicable, including simultaneous performance of at least some steps. Although the disclosure has been described in connection with specific examples, it should be understood that various changes, substitutions, and alterations apparent to those skilled in the art can be made to the disclosed embodiments without departing from the spirit and scope of the disclosure as set forth in the appended claims.

What is claimed is:

1. A computing system comprising:
   a storage configured to store time-series data of an operation of a machine; and
   a processor configured to
      predict a fatigue value of an operator of the machine via a predictive model that comprises a Rainflow counting algorithm that determines a degradation of the operator based on a changing attribute in the time-series data and a healing function that determines a healing component of the operator based on rest of the operator,
      wherein the processor is configured to predict the fatigue value by applying a decay function representing healing of the operator to the degradation of the operator determined by the Rainflow counting algorithm, and the processor is further configured to output information about the predicted fatigue value via a user interface.

2. The computing system of claim 1, wherein the predictive model is executed based on a rolling window of time-series data.

3. The computing system of claim 1, wherein the machine comprises one of an aircraft, a locomotive, an automotive vehicle, a submersible, a ship, an equipment for use in drilling or mining, and a healthcare machine.

4. The computing system of claim 1, wherein the time-series data comprises one or more of temperature, pressure, altitude, velocity, humidity, and noise, which are captured of the machine during operation.

5. The computing system of claim 1, wherein the healing component comprises a reduction in the degradation of the operator based on the non-operating time of the machine.

6. The computing system of claim 1, wherein the processor configured to output a graphical pattern of the predicted fatigue value over time which identifies the degradation and the healing component of the operator.

7. The computing system of claim 1, wherein the processor is configured to determine the degradation of the operator based on magnitudes of oscillations in the time-series data of the machine.

8. A method comprising:
   storing time-series data of an operation of a machine;
   predicting a fatigue value of an operator of the machine via a predictive model that comprises a Rainflow counting algorithm that determines a degradation of the operator based on a changing attribute in the time-series data and a healing function that determines a healing component of the operator based on rest of the operator, wherein the predicting the fatigue value comprises applying a decay function representing healing of the operator to the degradation of the operator determined by the Rainflow counting algorithm; and
   outputting information about the predicted fatigue value via a user interface.

9. The method of claim 8, wherein the predictive model is executed based on a rolling window of time-series data.

10. The method of claim 8, wherein the machine comprises one of an aircraft, a locomotive, an automotive vehicle, a submersible, a ship, an equipment for use in drilling or mining, and a healthcare machine.

11. The method of claim 8, wherein the time-series data comprises one or more of temperature, pressure, altitude, velocity, humidity, and noise, which are captured of the machine during operation.

12. The method of claim 8, wherein the healing component comprises a reduction in the degradation of the operator based on the non-operating time of the machine.

13. The method of claim 8, wherein the outputting comprises outputting a graphical pattern of the predicted fatigue value over time which identifies the degradation and the healing component of the operator.

14. The method of claim 8, wherein the predicting comprises determining the degradation of the operator based on magnitudes of oscillations in the time-series data of the machine.

15. A non-transitory computer-readable medium comprising instructions which when executed are configured to cause a computer to perform a method comprising:
   storing time-series data of an operation of a machine;
   predicting a fatigue value of an operator of the machine via a predictive model that comprises a Rainflow counting algorithm that determines a degradation of the operator based on a changing attribute in the time-series data and a healing function that determines a healing component of the operator based on rest of the operator, wherein the predicting the fatigue value comprises applying a decay function representing healing of the operator to the degradation of the operator determined by the Rainflow counting algorithm; and
   outputting information about the predicted fatigue value via a user interface.

16. The non-transitory computer-readable medium of claim 15, wherein the predictive model is executed based on a rolling window of time-series data.

17. The non-transitory computer-readable medium of claim 15, wherein the outputting comprises outputting a graphical pattern of the predicted fatigue value over time which identifies the degradation and the healing component of the operator.

18. The non-transitory computer-readable medium of claim 15, wherein the predicting comprises determining the degradation of the operator based on magnitudes of oscillations in the time-series data of the machine.

* * * * *